(12) United States Patent
Han et al.

(10) Patent No.: US 9,012,410 B2
(45) Date of Patent: Apr. 21, 2015

(54) METHOD OF TREATING INTRAUTERINE INFLAMMATION

(75) Inventors: Yiping Han, Beachwood, OH (US); Hongqi Liu, Wynnewood, PA (US)

(73) Assignee: Case Western Reserve University, Cleveland, OH (US)

( * ) Notice: Subject to any disclaimer, the term of this patent is extended or adjusted under 35 U.S.C. 154(b) by 570 days.

(21) Appl. No.: 12/519,335

(22) PCT Filed: Dec. 13, 2007

(86) PCT No.: PCT/US2007/087390
§ 371 (c)(1),
(2), (4) Date: Jun. 15, 2009

(87) PCT Pub. No.: WO2008/076804
PCT Pub. Date: Jun. 26, 2008

(65) Prior Publication Data
US 2010/0035829 A1    Feb. 11, 2010

Related U.S. Application Data

(60) Provisional application No. 60/874,758, filed on Dec. 13, 2006.

(51) Int. Cl.
*A61K 31/7028* (2006.01)
*A61K 31/7032* (2006.01)
*A61K 31/739* (2006.01)
*A61K 31/7034* (2006.01)

(52) U.S. Cl.
CPC ........... *A61K 31/739* (2013.01); *A61K 31/7028* (2013.01); *A61K 31/7034* (2013.01)

(58) Field of Classification Search
None
See application file for complete search history.

(56) References Cited

U.S. PATENT DOCUMENTS

2003/0139356 A1 *   7/2003   Persing et al. ............... 514/42
2007/0072824 A1     3/2007   Kawano et al.

FOREIGN PATENT DOCUMENTS

WO    WO 2006/138681 A2    12/2006

OTHER PUBLICATIONS

Hirsch, E. et al "The molecular pathophysiology of bacterially induced preterm labor . . ." J. Soc. Gynecol. Invest. (2005) vol. 12, pp. 145-155.*
Kemp, M. et al "Preterm birth, infection, and inflammation . . ." Reprod. Sci. (2010) vol. 17, No. 7, pp. 619-628.*
Adams Waldorf et al "Pre-treatment with Toll-like receptor 4 antagonist . . ." Reprod. Sci. (2008) vol. 15, No. 2, pp. 121-127.*
McDonald, H. et al "Antibiotics for treating bacterial vaginosis . . ." Cochrane Database Syst. Rev. (2007) vol. 1, pp. 1-63.*
Michalowicz, B. et al "Treatment of periodontal disease and the risk of premature birth" NEJM (2006) vol. 355, pp. 1885-1894.*
Cluff, Christopher W., et al., "*Synthetic Toll-Like Receptor 4 Agonists Stimulate Innate Resistance to Infectious Challenge*", Infection and Immunity, May 2005, p. 3044-3052.
Elovitz, Michael A., et al., *A New Model for Inflammation-Induced Preterm Birth—The Role of Platelet-Activating Factor and Toll-Like Receptor-4*, American Journal of Pathology, vol. 163, No. 5, Nov. 2003.
Fort, Madeline M., et al., "*A Synthetic TLR4 Antagonist Has Anti-Inflammatory Effects in Two Murine Models of Inflammatory Bowel Disease*", The Journal of Immunology, 2005, 174: 6416-6423.
Han, Yiping W., et al., "*Fusobacterium nucleatum Induces Premature and Term Stillbirths in Pregnant Mice: Implication of Oral Bacteria in Preterm Birth*", Infection and Immunity, Apr. 2004, p. 2272-2279.
Liu, Hongqi et al., "*Fusobacterium nucleatum Induces Fetal Death in Mice via Stimulation of TLR4-Mediated Placental Inflammatory Response*", The Journal of Immunology, 2007, 179: 2501-2508.
Stover, Alex G., et al., "*Structure-Activity Relationship of Synthetic Toll-like Receptor 4 Agonists*", The Journal of Biological Chemistry, vol. 279, No. 6, Issue of Feb. 6, pp. 4440-4449, 2004.
Wang, Hao, et al., "*Bacterially-Induced Preterm Labor and Regulation of Prostaglandin-Metabolizing Enzyme Expression in Mice: The Role of Toll-Like Receptor 4*", Biology of Reproduction 69, 1957-1963 (2003).

* cited by examiner

*Primary Examiner* — Leigh Maier

(74) *Attorney, Agent, or Firm* — Tarolli, Sundheim, Covell & Tummino LLP

(57) ABSTRACT

A method of treating intrauterine inflammation in a subject associated with intrauterine bacterial infection includes administering to the subject a therapeutically effective amount of a toll-like receptor 4 antagonist. The therapeutically effective amount administered to the subject is an amount effective in reducing intrauterine inflammation in the subject.

8 Claims, 8 Drawing Sheets

A

B

METHOD OF TREATING INTRAUTERINE INFLAMMATION

RELATED APPLICATION

This application claims priority from U.S. Provisional Application No. 60/874,758, filed Dec. 13, 2006, the subject matter, which is incorporated herein by reference.

GOVERNMENT FUNDING

This invention was made with government support under Grant No. NIH DE14924 awarded by the National Institutes of Health. The United States government has certain rights in the invention.

BACKGROUND

Preterm birth (PTB), defined as delivery before 37 wk of gestation, is a significant public health problem accounting for 70% of perinatal mortality and nearly half of long-term neurological morbidity (Goldenberg et al., (2000) N. Engl. J. Med. 342:1500-1507). The PTB rate in the United States is about 12% of all live deliveries, affecting a half-million babies and costing billions of dollars annually (Andrews et al., (2000) Am. J. Perinatol. 17:357-365).

Research has shown that intrauterine infections are highly prevalent among women who give birth prematurely (Chaim et al., (1992) Arch. Gynecol. Obstet. 259:51-58). The infecting organisms have been shown to originate from the lower genital tract and invade the pregnant uterus via an ascending mechanism or come from other parts of the body, such as the oral cavity, and reach the uterus through hematogenous transmission (Hill et al., (1998) Ann. Periodontol. 3:222-232).

The recent identification of an uncultivated oral species, *Bergeyella* species, in the amniotic fluid from a pregnancy complicated by premature delivery provides direct evidence in support of the oral-utero transmission (Han et al., (2006) J. Clin. Microbiol. 44:1475-1483). The *Bergeyella* species identified in amniotic fluid matched that found in the woman's dental plaque but was undetected in her vaginal sample (Hill et al., (1998)).

*Fusobacterium nucleatum* is one of the most prevalent species associated with intrauterine infection (Hill et al., (1998); Altshuler et al., (1985) Arch. Pathol. Lab. Med. 109: 739-743; Chaim and Mazor (1992) Arch. Gynecol. Obstet. 251:1-7; Hill et al., (1974) Infect. Immun. 9:599-603). It is a Gram-negative anaerobic oral species and an opportunistic human pathogen associated with various forms of periodontal disease. The organism can be isolated at a frequency of 10-30% from the amniotic fluid of women in preterm labor with intact membranes (Hill et al., (1993); Hill et al., (1998), Chaim et al., (1992); Cahill et al., (2005) Mol. Hum. Reprod. 11:761-766) and detected in 83% of PTB with premature rupture of membranes by PCR (Cahill et al., (2005)).

A causal relationship between *F. nucleatum* and adverse pregnancy outcome has been established in studies in mice. Hematogenous infection of pregnant mice by orally related *F. nucleatum* resulted in localized infections of the fetoplacental unit, leading to preterm and term stillbirths (Han et al., (2004) Infect. Immun. 72:2272-2279). The infections initiated at the decidua followed by spreading to the fetal membranes, amniotic fluid, and fetus, similar to the pattern observed in the ascending mechanism (Goldenberg et al., (2000), Han et al., (2004)). *F. nucleatum* is known to invade epithelial and endothelial cells in vitro (Han et al., (2005) J. Bacteriol. 187:5330-5340); its attachment and invasion of the endothelial cells have been observed in vivo in infected mouse placentas.

SUMMARY OF THE INVENTION

The present invention relates to a method of treating inflammation in a subject associated with intrauterine bacterial infection. The method includes administering to the subject a therapeutically effective amount of a toll-like receptor 4 antagonist. The therapeutically effective amount of toll-like receptor 4 antagonist administered to the subject is an amount effective in reducing intrauterine inflammation in the subject.

In one aspect of the invention, the toll-like receptor 4 antagonist can include a monophosphoryl lipid A analog. In another aspect of the invention the toll-like receptor 4 antagonist can include an aminoalkyl-glucosaminide-phosphate (AGP). In another aspect of the invention, the AGP can have the structure:

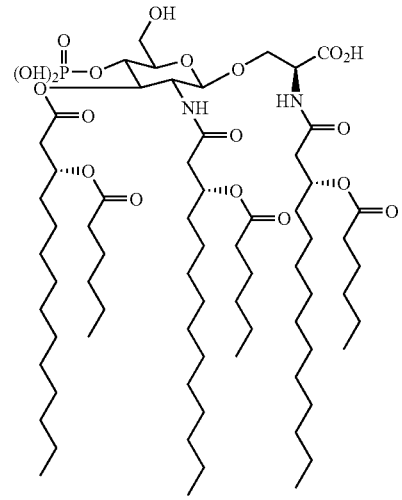

or a pharmaceutically acceptable salt or phosphate ester thereof.

The subject can be at risk of developing inflammation associated with intrauterine bacterial infection. The bacterial infection can include an intrauterine gram-negative infection (e.g., *Fusobacterium nucleatum*). The toll-like receptor 4 antagonist can be administered to the subject by parenteral, oral, or topical administration.

The present invention also relates to a method of treating a placental inflammation response associated with intrauterine bacterial infection. The method includes the step of administering to the subject a therapeutically effective amount of a toll-like receptor 4 antagonist. The therapeutically effective amount of toll-like receptor 4 antagonist administered to the subject is an amount effective in reducing placental inflammation in the subject.

In one aspect of the invention, the toll-like receptor 4 antagonist can include a monophosphoryl lipid A analog. In another aspect of the invention the toll-like receptor 4 antagonist can include an aminoalkyl-glucosaminide-phosphate (AGP). In another aspect of the invention, the AGP can have the structure:

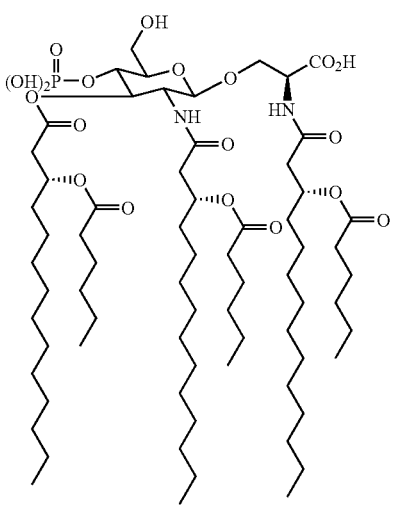

or a pharmaceutically acceptable salt or phosphate ester thereof.

The subject can be at risk of developing placental inflammation associated with intrauterine bacterial infection. The bacterial infection can include an intrauterine gram-negative infection (e.g., *Fusobacterium nucleatum*). The toll-like receptor 4 antagonist can be administered to the subject by parenteral, oral, or topical administration.

The present invention further relates to methods of inhibiting bacterial induced preterm birth, still birth, or fetal death. The method includes administering to a subject a therapeutically effective amount of a toll-like receptor 4 antagonist. The therapeutically effective amount of toll-like receptor 4 antagonist administered to the subject is an amount effective to reduce intrauterine inflammation and inhibit bacterial induced preterm birth, still birth, or fetal death.

In one aspect of the invention, the toll-like receptor 4 antagonist can include a monophosphoryl lipid A analog. In another aspect of the invention the toll-like receptor 4 antagonist can include an aminoalkyl-glucosaminide-phosphate (AGP). In another aspect of the invention, the AGP can have the structure:

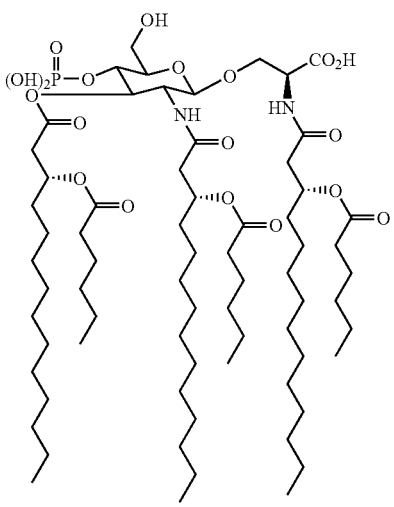

or a pharmaceutically acceptable salt or phosphate ester thereof.

The subject can be a mammalian subject that is at risk of developing bacterial induced preterm birth, still birth, or fetal death, such as a subject, which previous had a preterm birth, still birth, or fetal death. The toll-like receptor 4 antagonist can be administered to the subject by parenteral, oral, or topical administration.

The present invention yet further relates to a pharmaceutical composition for treating bacterial induced preterm birth, still birth, fetal death, and/or intrauterine inflammation. The pharmaceutical composition includes a therapeutically effective amount of a toll-like receptor 4 antagonist and an antibiotic. The therapeutically effective amount of toll-like receptor 4 antagonist is an amount effective to reduce intrauterine inflammation and inhibit bacterial induced preterm birth, still birth, or fetal death.

In an aspect of the invention the toll-like receptor 4 antagonist of the pharmaceutical composition can include a monophosphoryl lipid A analog. In another aspect of the invention the toll-like receptor 4 antagonist can include an aminoalkyl-glucosaminide-phosphate (AGP). In another aspect of the invention, the AGP can have the structure:

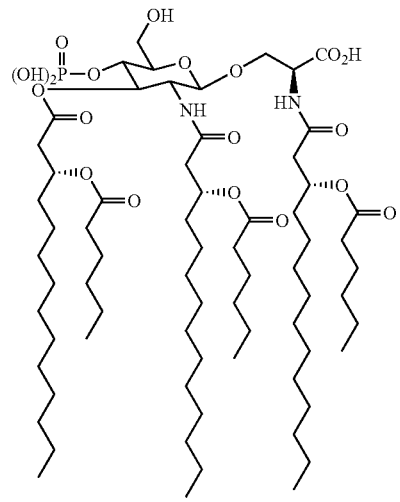

or a pharmaceutically acceptable salt or phosphate ester thereof.

injection of F. nucleatum 12230. The injection doses for each strain at each time point were also shown. Approximately 3-7×10$^7$ CFU were injected into each pregnant mouse. The live bacterial titers in each organ at 6, 16 (or 18), and 48 h post-bacterial injection were expressed as log$_{10}$ (CFU/gram tissue). A, C3H-HeN (■), n=11 (6 h), 8 (18 h), and 7 (48 h); C3H/HeJ (□), n=8 (6 h), 7 (18 h), and 6 (48 h). B, C57BL/6 (■), n=7 (6 h), 8 (16 h), and 7 (48 h); C57BL/6 TLR2$^{-/-}$ (◉), n=7 (6 h), 16 (16 h), and 5 (48 h); and C57BL/6 TLR4$^{-/-}$ (□), n=4 (6 h), 9 (16 h), and 8 (48 h). The SD is labeled above each bar. The asterisks indicate a significant difference of the bacterial titers between the wild-type and the mutant mice (*, p<0.05).

Figure 4A:
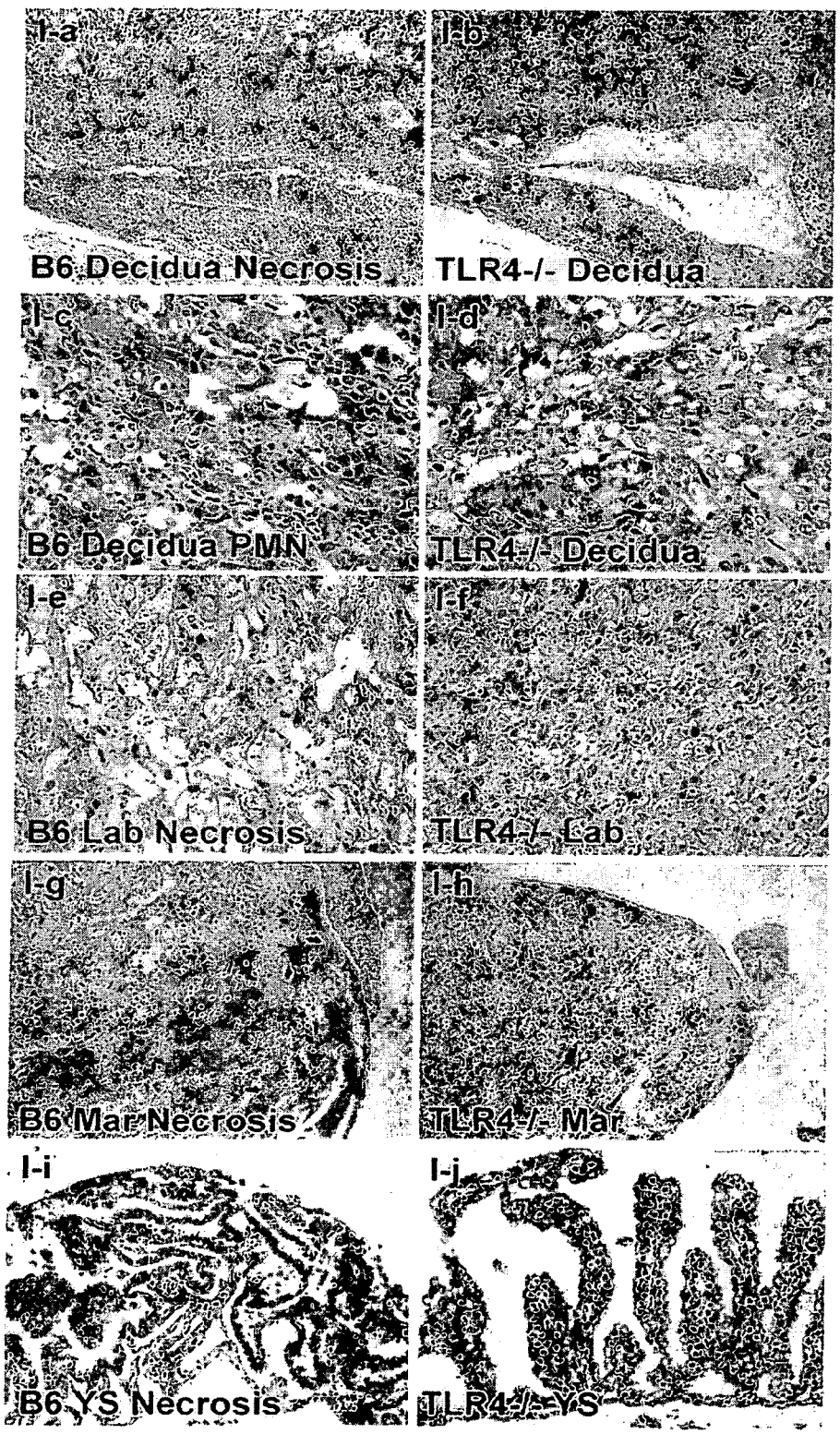
Figure 4B:
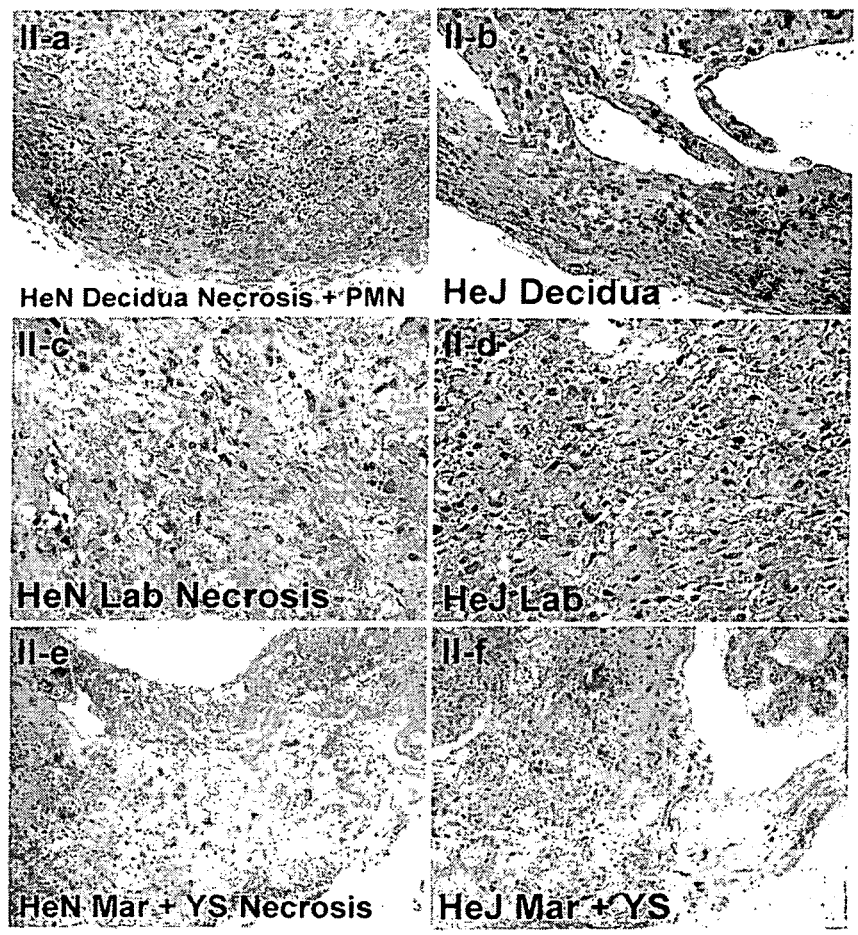

FIG. 4 illustrates histopathological analysis of murine fetoplacental units following F. nucleatum infection. I, Comparison of histopathological lesions in different utero regions of C57BL/6 (a, c, e, g, and i) and C57BL/6 TLR4$^{-/-}$ (b, d, f, h, and j) mice infected with F. nucleatum 12230 (original magnifications: X100 for a, b, g, and h; X200 for e and f; X400 for c and d; and X20 for i and j). II, Comparison of histopathological lesions in different utero regions of C3H/HeN (a, c, and e) and C3H/HeJ (b, d, and f) mice (original magnifications: X200 for a, b, c, and d; and X100 for e and f). The regions and lesions are indicated on the bottom of each photograph. B6, C57BL/6; PMN, polymorphonuclear cell; Lab, labyrinth; Mar; marginal (unction) region; YS, visceral yolk sac.

Figure 5:
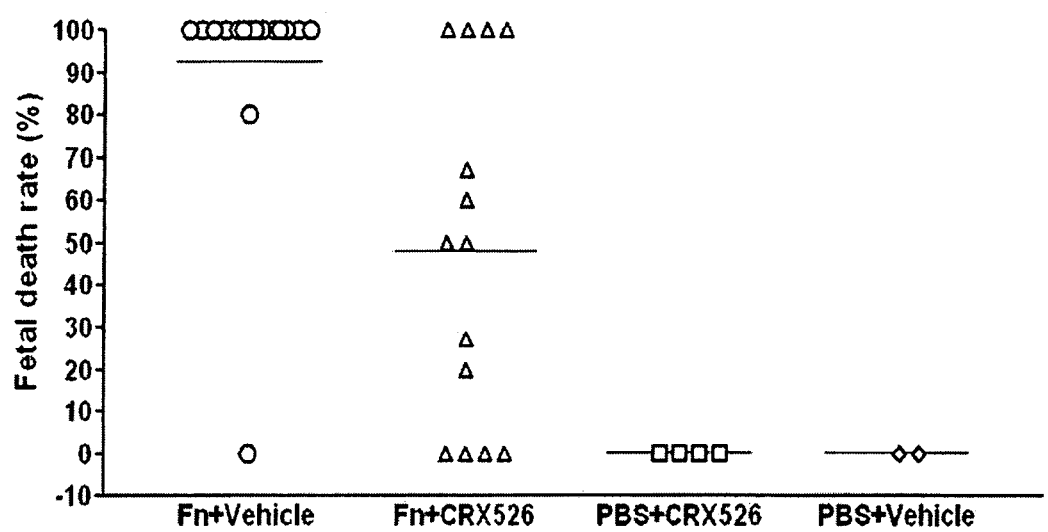

FIG. 5 illustrates the effect of TLR4A on the birth outcome of outbred CF-1 mice in response to F. nucleatum infection. On day 16, each pregnant CF-1 mouse received 1×10$^8$ CFU of F. nucleatum 12230 plus 100 μl of 2% glycerol (vehicle) (O; n=16), 1×10$^8$ CFU of F. nucleatum 12230 plus 0.1 mg of TLR4A in 100 μl of 2% glycerol (Δ; n=14), PBS plus 0.1 mg of TLR4A in 100 μl of 2% glycerol (ε; n=4), or PBS plus 100 μl of 2% glycerol (vehicle) (◊; n=2). On day 17, each mouse received a second dose of TLR4A or 2% glycerol as on the day before. The fetal death rate was expressed as percent dead fetuses of the total number of pups born to each mother. The horizontal lines indicate the average fetal death rate of each group. Fn, F. nucleatum 12230.

Figure 6:
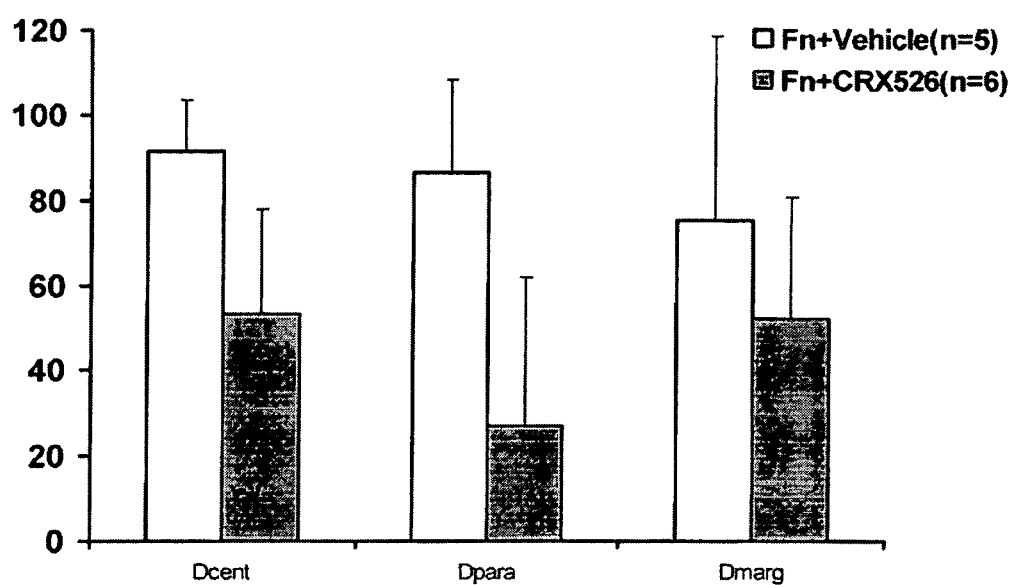

FIG. 6 illustrates the effect of TLR4A on decidual necrosis in response to fusobacterial infection. Placentas in the TLR4A-treated group (◉) and a placebo group (□) were harvested 48 h after F. nucleatum (Fn) injection. The percentage of placentas with necrosis in three different regions (central, paracentral, and marginal) in the decidua was calculated respectively for each pregnant mouse. Each bar represents the mean value for each group in each decidual region. The SD is labeled above each bar. n, Number of pregnant mice tested in each group. The asterisks indicate significant difference between the treatment and placebo group (*, p<0.05).

Figure 7:
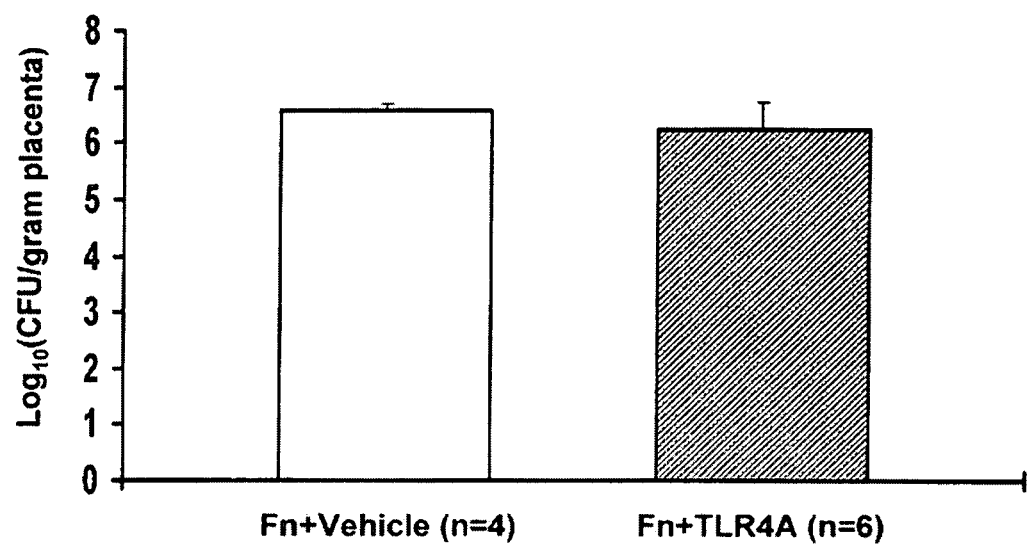

FIG. 7 illustrates the effect of TLR4A on F. nucleatum 12230 (Fn) colonization in the placentas of pregnant CF-1 mice. On day 16. each pregnant CF-1 mouse received either 1×10$^8$ CFU of F. nucleatum 12230 plus 100 μl of 2% glycerol (vehicle) (□, n=4) or 1×10$^8$ of CFU F. nucleatum 12230 plus 0.1 mg TLR4A in 100 μl of 2% glycerol (◉) n=6). On day 17 each mouse received a second dose of TLR4A or 2% glycerol as on the day before. On day 18, the mice were dissected to collect the placentas. The live fusobacterial titer was determined and expressed as log$_{10}$ (CFU/g placental tissue). The SD is expressed above each bar.

DETAILED DESCRIPTION

The present invention relates generally to methods and pharmaceutical compositions for treating intrauterine inflammation associated with intrauterine bacterial infection as well as preterm birth, still birth, and/or fetal death associated with intrauterine bacterial infection. Intrauterine infection plays a pivotal role in preterm birth (PTB), still birth, and fetal death, and is characterized by intrauterine inflammation resulting from infiltration by causative bacterial agents.

"Preterm birth" as used herein, relates to delivery before the 37 week of gestation in a human subject. Intrauterine bacterial infection plays an important role in preterm birth, with the infection rate inversely related to the gestational age (Andrews et al., (2000); Hill et al., (1993) Clin. Infect. Dis. 16(Suppl. 4): S423-S424; Hill et al. (1998) Ann. Periodontaol. 3:222-232; Romero et al., (1991) Ann. NY Acad. Sci. 622:355-375; Watts et al., (1992) Obstet. Gynecol. 79:351-357). While preterm birth does not necessarily lead to the death of the subject's offspring, it can lead to morbidity (Goldenberg et al., (2000) N. Engl. J. Med. 342:1500-1507).

The term "still birth" as used herein, relates to a fetus which has died in the uterus or during labor or delivery exiting a subject's body. The term is often used in distinction to a live birth or miscarriage. The term "still birth" can more specifically relate to a fetus which has died after reaching mid-second trimester to full term gestational age. For example, "still birth" can be used to describe an infant delivered without life after 22-24 weeks gestation. The term "miscarriage" is often used if the death occurs earlier in fetal development.

The term "fetal death" as used herein, relates to death prior to the complete expulsion or extraction from its mother of a product of conception, irrespective of the duration of pregnancy and which is not an induced termination of pregnancy. The death is indicated by the fact that after such expulsion or extraction, the fetus does not breathe or show any other evidence of life, such as beating of the heart, pulsation of the umbilical cord, or definite movement of voluntary muscles. Heartbeats are to be distinguished from transient cardiac contractions; respirations are to be distinguished from fleeting respiratory efforts or gasps. The term fetal death as used herein is meant to encompass fetal death from miscarriage.

A variety of gram-negative pathogens have been isolated from the placenta, amniotic fluid and chorioamnion cultures, with *Fusobacterium nucleatum, Ureaplasma urealyticum, Mycoplasma hominis*, and *Bacteroides urealyticus* being the most prevalent species. Among the bacterial species listed above, *U. urealyticum, M. hominis*, and *B. urealyticus* are opportunistic pathogens indigenous to the female lower genital tract and often associated with bacterial vaginosis, which is recognized as a risk factor for preterm birth (Chaim et al., (1997) Arch. Gynecol. Obstet. 259:51-58; Hill et al., (1998) Ann. Periodontol. 3:222-232; Yoon et. al., (2000) Am. J. Obstet. Gynecol. 183:1130-1137). *U. urealyticum, M. hominis*, and *B. urealyticus* and certain other species commonly found in the lower genital tract are transmitted to the uterus through the ascending route to infect the fetoplacental unit.

Additional gram-negative pathogens in the female genital tract contemplated by the methods of the present invention include *Escherichia coli, Proteus mirabilis, Proteus vulgaris*, and *Pseudoinonas pyocyaneus*.

*F. nucleatum*, a filamentous gram negative anaerobe, however is an oropulmonary pathogen that is infrequently found in the vaginal tract. Although associated with bacterial vaginosis, *F. nucleatum* is relatively uncommon compared to the frequencies of other species linked to the disease (Hillier et al., (1993) Clin. Infect. Dis. 16(Suppl. 4):S273-S281). *F.* nucleatum is ubiquitous in the oral cavity and is one of the most abundant species in subgingival plaque. The frequency of *F. nucleatum* infection in amniotic fluid is approximately 10 to 30% in women in preterm labor with intact membranes and 10% in women with preterm premature rupture of membranes, in considerable excess compared to most other single species (Chaim et al., (1992) Arch. Gynecol. Obstet. 251:1-7; Hill et al., (1998) Ann. Periodontol 3:222-232). The species of *Fusobacterium* most frequently isolated from the lower genital tract, *F. naviforme* and *F. gonidiaformans*, are rarely isolated from amniotic fluid cultures, suggesting that *F. nucleatum* in the oral cavity may spread hematogenously to infect the pregnant uterus (Han et al., (2004) Infect. and Immun. 72:2272-2279). Additionally, it has been found that the oral bacteria *Porphyromonas gingivalis* was disseminated systemically in pregnant mice, bacterial DNA was detected in the murine placentas associated with intrauterine growth restriction (Lin et al., (2003) Infect. Immun. 71:5163-5168).

It was discovered that gram negative anaerobic bacteria once inside the pregnant uterus can stimulate the synthesis and release of proinflammatory cytokines, the infiltration and activation of neutrophils, and the synthesis and release of metalloproteinases and prostaglandins that can lead to cervical ripening, membrane weakening and rupture, and the initiation of uterine contractions. This response is due in part to the presence of Toll-like receptors on the intrauterine mammalian cell membranes. In particular, Grain-negative bacteria were found to induce an intrauterine proinflammatory cytokine response via Toll-like receptor 4 (TLR4). A TLR4 antagonist was also found to be effective in reducing decidual necrosis and fetal death without affecting bacterial colonization in the placenta.

One aspect of the present invention therefore relates to a method of treating intrauterine inflammation, such as an inflammatory placental response, by administering to a a mamalian subject a therapeutically effective amount of at least one TLR4 antagonist. The therapeutically effective amount can be an amount effective to reduce intrauterine inflammation and to mitigate preterm birth, still birth, or fetal death.

The mammalian subject can include without limitation, a human, a non-human primate, a mouse, a rat, a guinea pig, a rabbit, a cat, a dog, a horse, a cow, a sheep, a goat, a pig, etc. In the case of the present invention, the subjects contemplated are mammals expressing TLRs on their cell membranes. More specifically, mammals expressing TLR4 on their cell membranes.

In an aspect of the invention, the TLR4 antagonists used for treating intrauterine inflammation, preterm birth, still birth, and/or fetal death can include synthetic monosacharide lipid A mimetics. Examples of monosacharide lipid A mimetics are aminoalkyl-glucosamide-phosphates (AGPs). AGPs are synthetic monosaccharide lipid A mimetics of a biologically active hexa-acylated component present in the widely used adjuvant monophosphoryl lipid A (MPL adjuvant). Because AGPs are prepared by chemical synthesis, it is possible to synthesize molecules with defined modifications in the acyl chain length (Stover et al., (2004) J. Biol. Chem. 279(6); 4440-4449).

According to an aspect of the present invention, TLR4 receptor activation is blocked by administration of a TLR4 antagonist, leading to beneficial effects in the treatment of inflammation associated with intrauterine bacterial infection. TLR4 antagonists for use in the present invention can include AGPs, especially AGPs which do not stimulate cytokine production or other gene expression in human peripheral blood monocytes in vitro or induce an inflammatory response in vivo.

In another aspect of the invention, the TLR4 antagonists utilized in the methods of the invention can be, for example, analogs of the lipid A region of LPS. In one example, the TLR4 antagonist can of the present invention can include an AGP having the following general structure:

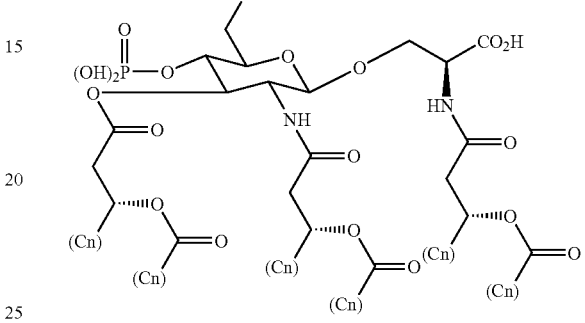

wherein the "n" can be any positive integer.

In another example, the AGP can have the following structure:

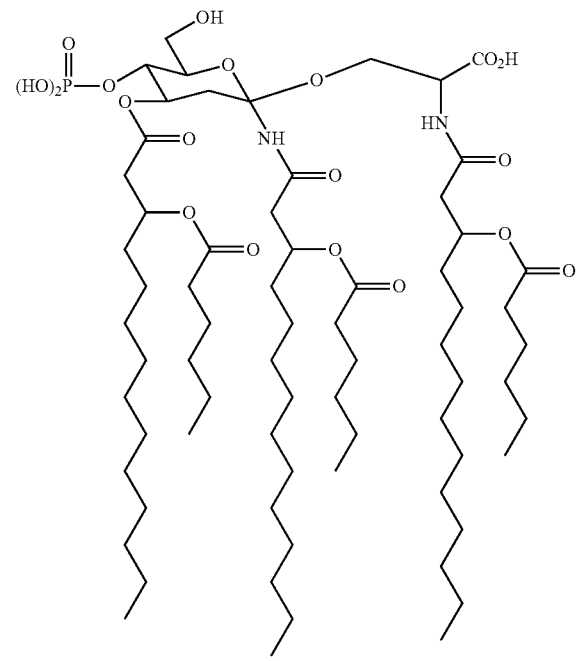

The above identified AGP is commercially available from Glaxo Smith Kline (UK) under the tradename CRX 526.

Additional examples of lipid A analogs which can be used in the methods of the present invention include lipid A analogs having the following structure:

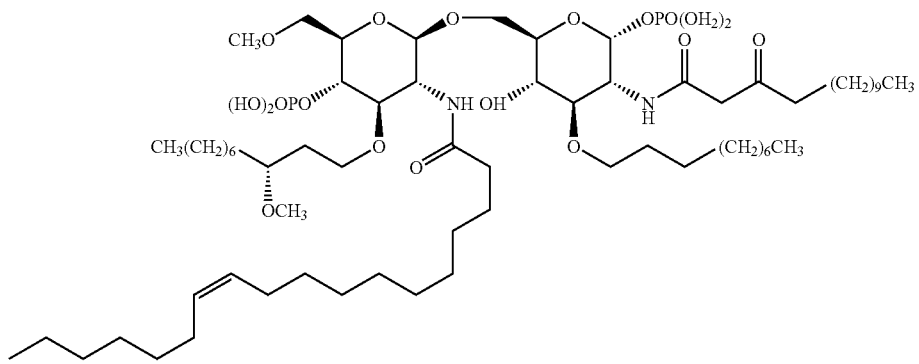

or a pharmaceutically acceptable salt thereof.

In a more specific example the compound can have the following structure:

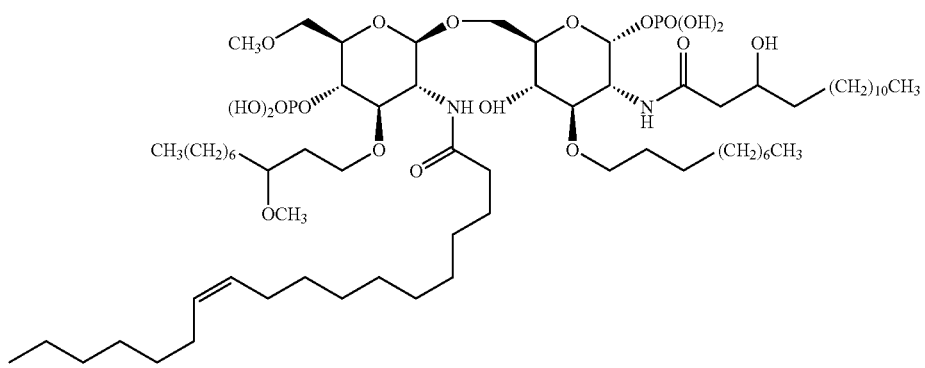

or a pharmaceutically acceptable salt thereof. This compound is known as eritoran (also known as compound E5664, compound 1287, and SGEA) and is described in U.S. Pat. No. 5,935,938.

Additional examples of compounds that can be used in the methods of the present invention include the following:

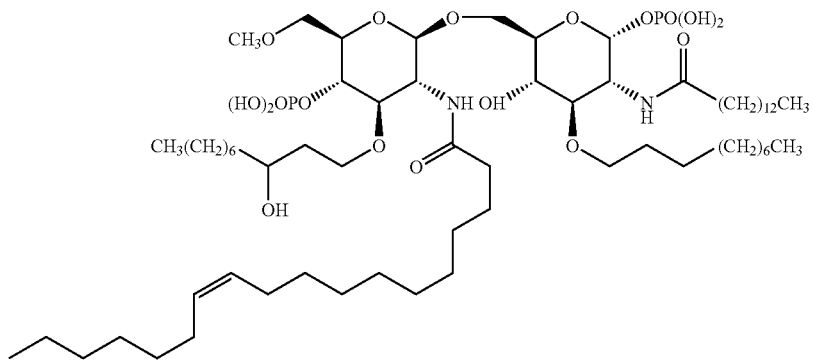

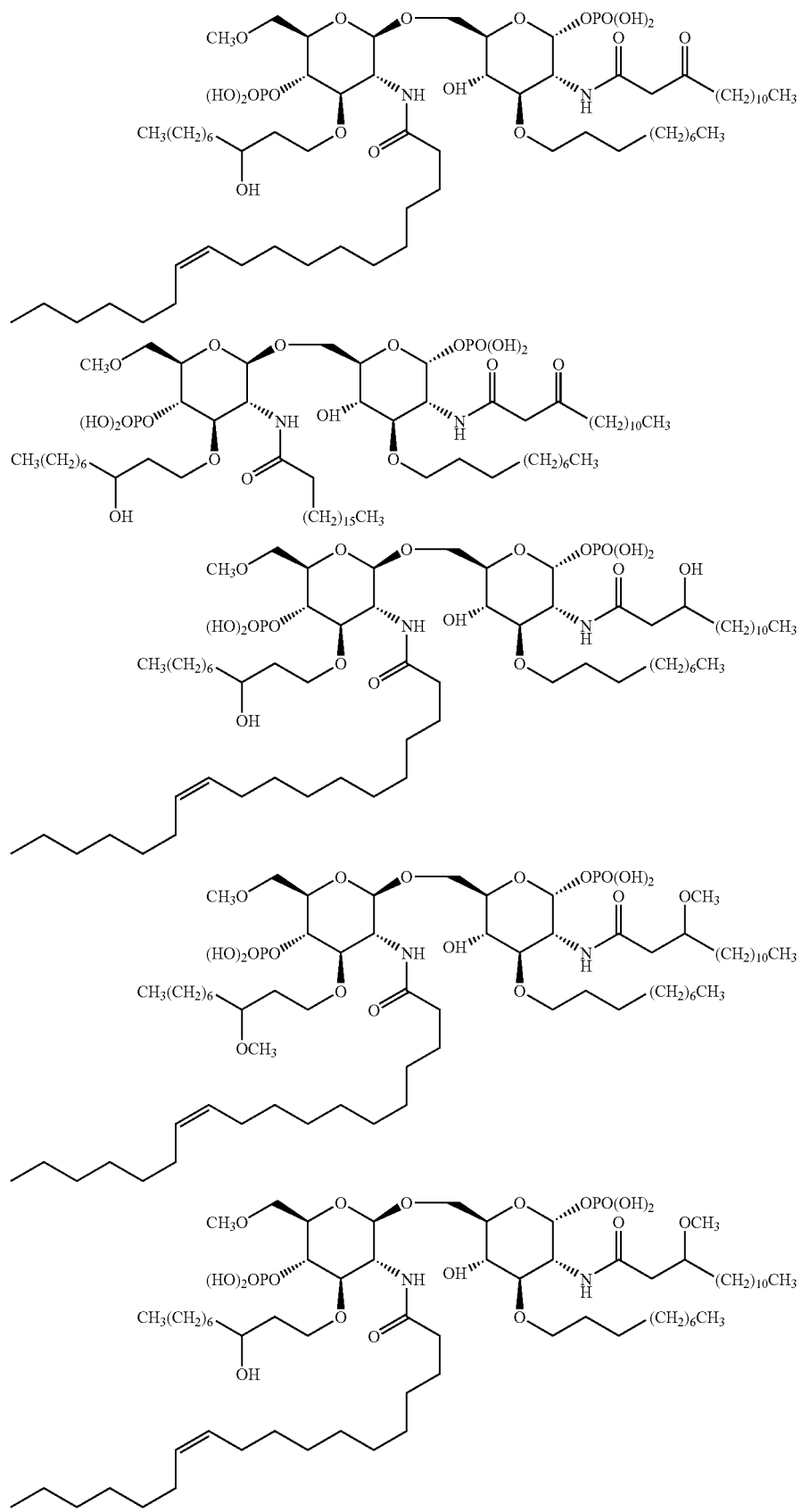

and pharmaceutically acceptable salts thereof (see U.S. Pat. App. No. 2007/0072824A1).

The pharmaceutically acceptable salts of the TLR4 antagonists of the invention are not particularly limited. Examples thereof include, but are not limited to, acid addition salts formed by reacting the compounds of the invention with pharmaceutically acceptable acids.

Additional TLR4 antagonists that can be used in the invention include, for example, compound B351 (U.S. Pat. No. 5,530,113), as well as other compounds described in the following patents: U.S. Pat. Nos. 5,935,938; 5,612,476; 5,756,718; 5,843,918; 5,750,664; 6,235,724; 6,184,366; and 5,681,824. Methods for making these compounds are also described within these documents. Additional methods for making such drugs are described, for example, in WO 02/94019.

Additionally, the TLR4 antagonist can include a TLR4 inhibitor. For example, a TLR4 polypeptide sequence that corresponds to at least a portion of the TLR4 receptor and binds TLR4 ligand during TLR4 signal transduction event. Other examples include a non-TLR4 protein or polypeptide that inhibits TLR4 activity, a small molecule inhibitor of TLR4 activity, or an inhibitory ligand that is a variant of the natural ligand of TLR4, namely bacterial bacterial lipopolysaccharide (e.g. analogs of the lipid A region of LPS as described above). Regardless of the type of TLR4 inhibitor employed, the TLR4 inhibitor is administered to achieve transient blockade of TLR4 function, thereby neutralizing or at least partially inhibiting the effect of TLR4 on inflammation associated with intrauterine bacterial infection.

Examples of polypeptide fragments of the TLR-4 may include at least a portion of the receptor sequence that binds to a TLR-4 ligand, are preferably short polypeptides from about 10 to 100 or 10 to 50 aa in length (or smaller), which contain the TLR-4 ligand binding domain. The peptide fragments can also be part of an N-terminal or C-terminal fusion protein. The full length sequence of various human TLR-4 isoforms are known (see Genbank Accession Nos. NP_6 12564 (isoform A), NP_6 12566 (isoform B), NP_003257 (isoform C), and NP_6 12567 (isoform D), each of which is hereby incorporated by reference in its entirety). Sequences for other mammalian TLR4 homologs are also known, including those of mouse, rat, orangutan, etc.

Non-TLR-4 protein or polypeptide inhibitors of TLR-4 have also been identified in the literature, and these can be used. Two such inhibitors are identified in Yang et al., "Novel TLR-4 Antagonizing Peptides Inhibit LPS-induced Release of Inflammatory Mediators by Monocytes," Biochem. Biophys. Res. Commun. 329.3):846-54 (2005), which is hereby incorporated by reference in its entirety; and chemokine receptor 4 and its ligand have also been shown to be effective (Kishore et al., "Selective Suppression of Toll-like Receptor 4 Activation by Chemokine Receptor 4," FEBS Lett. 579(3): 699-704 (2005), which is hereby incorporated by reference in its entirety).

Other examples of TLR-4 antagonists include, without limitation, Rhodobacter sphaeroides lipid A, which is a specific antagonist of TLR-4; E5564 (also known as compound 1287, SGEA, and Eriforan) (Mullarkey et al., "Inhibition of Endotoxin Response by E5564, a Novel Toll-like Receptor 4-directed Endotoxin Antagonist," J. Pharmacol. Exp. Ther. 304(3):1093-1102 (2003); Hawkins et al., "Inhibition of Endotoxin Response by Synthetic TLR4 Antagonists," Curr Top Med Chem. 4(11):1 147-1171 (2004); U.S. Pat. No. 5,681,824 to Christ et al., each of which is hereby incorporated by reference in its entirety); TAK-242 (Ii et al., "A Novel Cyclohexene Derivative, (TAK-242), Selectively Inhibits Toll-like Receptor 4-mediated Cytokine Production Through Suppression of Intracellular Signaling," Mo. Pharmacol. 69(4): 128 8-95 (2006), which is hereby incorporated by reference in its entirety); the endogenous TLR-4 inhibitor RP1OS (Divanovic et al., "Inhibition of TLR-4/MD-2 signaling by RP1O5/MD-1," J. Endotoxin Res. 11(6) :363-368 (2005), which is hereby incorporated by reference in its entirety); the lipid A-mimetic CRX-526 (Fort et al., "A Synthetic TLR4 Antagonist Has Anti-Inflammatory Effects in Two Murine Models of Inflammatory Bowel Disease," J. Immunol 174:6416-6423 (2005), which is hereby incorporated by reference in its entirety); CyP, a natural LPS mimetic derived from the cyanobacterium Oscillatoriaplanktothrix FP1 (Macagno et al., "A Cyanobacterial LPS Antagonist Prevents Endotoxin Shock and Blocks Sustained TLR4 Stimulation Required for Cytokine Expression," J. Exp. Med. 203 (6):1481-1492 (2006), which is hereby incorporated by reference in its entirety; a phenol/water extract from T. socranskii subsp. socranskii (TSS-P) (Lee et al., "Phenol/water Extract of Treponema socranskii subsp. socranskii as an Antagonist of Toll-like Receptor 4 Signaling," Microbiol. 1 52(2):535-46 (2006), which is hereby incorporated by reference in its entirety); CLR proteins such as Monarch-i (Williams et al., "The CATERPILLER Protein Monarch-i Is an Antagonist of Toll-like Receptor-, Tumor Necrosis Factor alpha-, and *Mycobacterium tuberculosis*-induced pro-inflammatory signals," J. Biol. Chein. 280(48):39914-39924 (2005), which is hereby incorporated by reference in its entirety); and small molecule TLR-4/TLR-2 dual antagonists, such as ER81 1243, ER81121 i, and ER81 1232 (U.S. Patent Application Pubi. No. 20050113345 to Chow et al., which is hereby incorporated by reference in its entirety). Further examples of TLR4 inhibitors or antagonists can be found in WO2006/138681A2 and are incorporated herein by reference.

According to the methods of the invention, a TLR4 antagonist is administered to a subject suffering from inflammation associated with an intrauterine bacterial infection. TLR4 antagonists such as those noted above can be administered using standard methods including, for example, parenteral, subcutaneous, intravenous, intraarticular, intrathecal, intramuscular, intraperitoneal, or intradermal injections, or by transdermal, buccal, oromucosal, oral routes or via inhalation. The particular approach and dosage used for a particular subject depends on several factors including, for example, the location(s) of any discomfort, and the general health of the patient. Based on factors such as these, a medical practitioner can select an appropriate approach to treatment.

Treatment according to the present methods of the invention can be altered, stopped, or re-initiated in a subject depending on the status of inflammation associated with intrauterine bacterial infection. Treatment can be carried out as intervals determined to be appropriate by those of skill in the art. For example, the administration can be carried out 1,2,3 or 4 times a day.

Determination of a therapeutically effective amount is within the capability of those skilled in the art. The exact formulation, route of administration, and dosage can be chosen by the individual physician in view of the subject's condition. The term "therapeutically effective amount" refers to an amount (dose) effective in treating a subject, having, for example, inflammation associated with intrauterine bacterial infection. It is also understood herein that a "therapeutically effective amount" may be interpreted as an amount giving a desired therapeutic effect, wither taken into one dose or in any dosage or route or taken alone or in combination with other therapeutic agents. In the case of the present invention, a "therapeutically effective amount" may be understood as an amount of TLR4 antagonist to reduce inflammation associated with intrauterine bacterial inflammation.

Formulation of the pharmaceutical compounds for use in the modes of administration noted above (and others) are known in the art and are described, for example, in Remington's Pharmaceutical Sciences (18$^{th}$ edition), ed. A. Gennaro, 1990, Mack Publishing Company, Easton, Pa. (also see, e.g., M. J. Rathbone, ed., Oral Mucosal Drug Delivery, Drugs and the Pharmaceutical Sciences Series, Marcel Dekker, Inc., N.Y., U.S.A., 1996; M. J. Rathbone et al., eds., Modified-Release Drug Delivery Technology, Drugs and the Pharmaceutical Sciences Series, Marcel Dekker, Inc., N.Y., U.S.A., 2003; Ghosh et al., eds., Drug Delivery to the Oral Cavity, Drugs and the Pharmaceutical Sciences Series, Marcel Dekker, Inc., N.Y., U.S.A., 2005; and Mathiowitz et al., eds., Bioadhesive Drug Delivery Systems, Drugs and the Pharmaceutical Sciences Series, Marcel Dekker, Inc., N.Y., U.S.A., 1999.

All patients, and in particular those affected with intrauterine bacterial infection (or at risk of intrauterine bacterial infection) which not readily accessible or suitable for topical administration, can be treated by a systemic approach, such as intravenous infusion. For example, the drug can be administered at a low dosage by continuous intravenous infusion. In another example, in which a patient requires longer-term care, the drug can be administered intermittently (e.g., every 12-24 hours). In a variation of this approach the initial or loading dose can be followed by maintenance doses that are less than (e.g., half) the loading dose or by continuous infusion. The duration of such treatment can be determined by those of skill in the art, based on factors such as, for example, the severity of the condition and the observation of improvements. Additional details concerning the use of infusion to administer TLR4 antagonists, such as eritoran, are provided in US-2003-0105033-A1 (bolus or intermittent infusion) and WO 00/41703 (continuous infusion), the contents of each of which are incorporated herein by reference.

When administering the TLR4 antagonist to the subject by intravenous infusion, it is preferable to use devices and equipment (e.g., catheters, such as central or peripheral venous catheters, tubing, drip chambers, flashback bulbs, injection Y sites, stopcocks, and infusion bags) that are compatible with the drug. In particular, catheters including a chlorhexidine-based antimicrobial coating have been found to disrupt the size of the micelles of the drug that are formed during formulation, leading to inadequate concentrations in blood. Thus, it is preferable to use devices and equipment that have, for example, a non-clorhexidine-based antimicrobial coating, such as an antimicrobial coating that includes one or more other antibiotics, such as rifampin or minicyclin.

The TLR4 antagonists can be administered to subjects by any acceptable manner known in one skilled in the art, including topically (e.g., by gel, rinse, lozenge, cream, ointment, or patch), by intravenous infusion, orally (e.g., by tablet, capsule, lozenge, cream, cream, ointment or patch), or vaginally (e.g., by cream, ointment, gel, or suppository). Also, treatment according to the invention can be carried out in combination with other approaches to treating inflammation associated with intrauterine bacterial infection, including antimicrobial and palliative treatments, as is discussed further below.

Subjects which can be treated according to the methods of the present invention include those who have inflammation associated with intrauterine bacterial infection. In addition, subjects who do not have, but are at risk of developing inflammation associated with intrauterine bacterial infection can be treated according to the present invention. In the latter group of subjects, the treatment can inhibit or prevent the development of inflammation associated with intrauterine bacterial infection. For example, a subject with a medical history of intrauterine bacterial infection, preterm birth, still birth, or fetal death, can be treated according to the methods of the present invention.

Inflammation of the placenta is typically secondary to infection of the placental membranes. *F. nucleatum* colonization in the placenta has been shown to be accompanied by inflammation similar to intrauterine infections in humans, suggesting placental inflammatory response as an important factor in the pathogenesis of bacterial-induced PTB (Han et al., (2004)). It is also well known that placental inflammation is associated with a poor clinical outcome for both the mother and the fetus, including major perinatal morbidities such as sepsis, respiratory distress syndrome, and CNS damage. Therefore, another aspect of the present invention relates to methods of treating placental inflammation response associated with intrauterine bacterial infection. The methods include the step of administering to the subject a therapeutically effective amount of a toll-like receptor 4 antagonist. The therapeutically effective amount administered to the subject is the amount effective in reducing placental inflammation in the subject. All of the delivery methods and formulations described herein are contemplated by this aspect of the present invention.

In accordance with another aspect of the invention, methods of inhibiting bacterial induced preterm birth, still birth, or fetal death include the step of administering to a subject a therapeutically effective amount of a toll-like receptor 4 antagonist. The therapeutically effective amount administered to the subject is the amount effective in inhibiting bacterial induced preterm birth, still birth, or fetal death. All of the delivery methods and formulations described herein are contemplated by this aspect of the present invention.

The present invention further relates to the use of TLR4 antagonists in a combination therapy for treating inflammation in a subject associated with intrauterine bacterial infection.

The phrase "combination therapy" embraces the administration of TLR4 antagonist, and a therapeutic agent as part of a specific treatment regimen intended to provide beneficial effect from the co-action of these therapeutic agents. Administration of these therapeutic agents in combination typically is carried out over a defined time period (usually minutes, hours, days or weeks depending upon the combination selected). "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. The sequence in which the therapeutic agents are administered is not narrowly critical.

In an aspect of the invention, the therapeutic agent administered in combination with a TLR4 antagonist can include antibiotics or other anti-microbial medications safe for use in a subject during pregnancy. For example, the additional agents can include, but are not limited to, penicillins, nystatin vaginal (Mycostatin), amoxicillin, ampicillin, augmentin (amoxicillin-clavulantate), Dicloxicillin, Macrobid (nitrofurantoin), Flagyl (metronidazole), Cephalosporins, Duricef (cefadroxiI), Cleocin (clindamycin), Erythromycin, Zithromax (azithromycin), Famzir (famciclovir), Zovirax (acyclovir), Valtrex (valacyclovir), Clotrimazole vaginal (Mycelex, Lotrimin), bactrim, trimethoprim, Biaxin (clarithromycin), Cipro (ciprofloxacin), Diflucan (fluconazole), Monistat (miconazole), Terazol (terconazole), quinacrinc, chloroquine, pyrimethamine, trimethoprim, primaquine, Isoniazid, Rifampin, and Vermox (mebendazole).

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE

Bacterial and Mouse Strains and Cell Lines

*Fusobacterium nucleatum* 12230 was maintained as previously described (Han et al., (2006) Current Protocols in Microbiology John Wiley and Sons, New York). C57BL/6, C3H/HeN, and C3H/HeJ mice were purchased from the National Cancer Institute (Bethesda, Md.). C57BL/6 TLR2$^{-/-}$ and C57BL./6 TLR4$^{-/-}$ mice (Hoshino et al., (1999) J. Immunol. 162:3749-3752; Takeuchi et al., (1999) Immunity 11: 443-451) were obtained from Drs. S. Akira (Osaka University, Osaka, Japan) and A. Hise (Case Western Reserve University, Cleveland, Ohio). All mice were kept in sterilized filtered-topped cages, fed autoclaved food and water, and handled in a laminar flow hood in a BSL2 room. HEK293-null, HEK293/human TLR2 (hTLR2), and HEK293/hTLR4/MD2/CD14 cells were obtained (InvivoGen, California). The cells were maintained at 37° C. in 5% $CO_2$ in DMEM medium with high glucose (4.5 g/L) (Mediatech, Virginia) supplemented with 10% FBS (Invitrogen Life Technologies, California) and the antibiotics blasticidin S at 10 µg/ml, HygroGold at 50 µg/ml, and Normocin at 100 µg/ml, all from InvivoGen.

In vitro Activation of the HEK293 Cells

HEK293 or HEK293/hTLR2 and HEK293/hTLR4/MD2/CD14, were seeded into 96-well plates at a density of 50,000 cells/well and allowed to grow overnight. The cells were then incubated with and N-palmitoyl(S)-[2,3-bis(palmitoyloxy)-(2, RS)-propyl]-Cys-Scr-Lys4 (Pam3CSK4), ultrapure *Escherichia coli* LPS, or fresh cultures of *F. nucleatum* 12230 at the indicated doses followed by a 24-h incubation. The supernatant was harvested and centrifuged and the amount of IL-8 secreted was determined by ELISA.

Elisa

Immunlon flat-bottom 96-well microliter plates (Thermo Electron, Mass) were coated with goat anti-human IL-8 Ab (4 µg/ml; R&D System) in 100 µl of coating buffer (0.05 M carbonate buffer (pH 9.6)). After overnight incubation at 4° C., the plates were washed six times with washing buffer, i.e., 0.05% Tween 20 in PBS (Sigma-Aldrich), followed by an overnight incubation in blocking buffer (1% BSA in PBS) at 4° C. The plates were washed four times before an aliquot of 100 µl of diluted mammalian cell culture supernatant or human IL-8 (R&D Systems, Minn) were added to each well and incubated overnight at 4° C. The plates were washed, followed by 3-h incubation with polyclonal rabbit anti-human 11,-8 Ab (1/1000; Endogen) at room temperature. After the plates were washed, a HRP-conjugated goatanti-rabbit IgG Ab (1/2500; BioSource International) was added and incubated for 1.5 h at room temperature. After the final wash, 100 µl of tetramethylbenzidine (Pierce) was added to each well. The color reaction was stopped by adding 100 µl of 2 M sulfuric acid. The light absorbance was measured at 450 nm on a Bio-Rad Model 680 microplate reader. The experiment was performed in triplicate and repeated multiple times.

Mating i.v. Injection of Mice and Kinetics of Infection

Mating and i.v. injection of *F. nucleatum* 12230 were conducted as previously described (Han et al., (2004)). Briefly, 10-wk-old mice were caged together at a female-to-male ratio of 2:1. Mating was determined by the presence of a white vaginal plug. The day when the plug was detected was termed day 1 of gestation. Pregnant mice were infected on day 16 or 17 of gestation. Cultures of *F. nucleatum* 12230 were washed once with sterile PBS. Based on its OD at 600 nm, the cultures were adjusted so that the estimated titer was ~$10^8$ CFU/ml. The actual CFU was determined by plating serial dilutions of the culture suspension onto blood agar plates. An aliquot of 100 µl of the bacterial suspension was injected into the tail vein of each mouse. The birth outcome was recorded. For kinetics of infection, groups of 4-16 mice were sacrificed at each indicated time postinjection. The liver, spleen, and placentas were harvested from each pregnant mouse, weighed, and homogenized in sterile PBS. Full thickness cross-sections of the placenta and underlying uterus were obtained on 2-5 placentas per animal in each experimental group. The live bacterial titer was determined by plating serial dilutions on blood agar plates. The bacterial titer was expressed as $\log_{10}$ (CFU/grain tissue). In the TLR4A treatment experiment, ~$1\times10^8$ CFU of *F. nucleatum* 12230 in 100 µl of PBS were mixed with either 0.1 mg of TLR4A in 100 µl of vehicle (2% glycerol) or 100 µl of 2% glycerol and injected through tail veins on day 16 of gestation. On day 17, a second dose of 0.1 mg of TLR4A in 100 µl of 2% glycerol or 100 µl of 2% glycerol alone was injected. For controls, TLR4A or its vehicle was injected into pregnant CF-1 in the absence of *F. nucleatum* 12230.

Histopathological Analysis of Infected Fetoplacental Units

The histopathological analysis was conducted as previously described (Han et al., (2004)). Full thickness H&E-stained sections were examined in a blinded fashion by a pathologist (R.W.R.) as before (Han et al., (2004)). For each specimen, necrosis and inflammation (polymorphonuclear leukocytes) were evaluated in three decidual regions (margin, center, and paracentral venous sinusoidal), three placental regions (spongiotrophoblast, labyrinth, and chorioallantoic plate), and two regions of the placental membranes (yolk sac and amnion) (Han et al., (2004)). Data are presented as the group mean±SD of the percentage of positive regions divided by the total number of regions sampled for each mouse.

Statistical Analysis

All results arc expressed as the mean value±SD. The nonparametric Mann-Whitney U test was used for comparison of fetal death rates and the decidual necrosis, and the Student t test was used for the bacterial titers (SPSS 12.0.1 for Windows). Differences between groups were considered significant with $p<0.05$.

Results

F. nucleatum 12230 Stimulates IL-8 Expression via Human TLR2 and TLR4 in vitro

Figure 1:
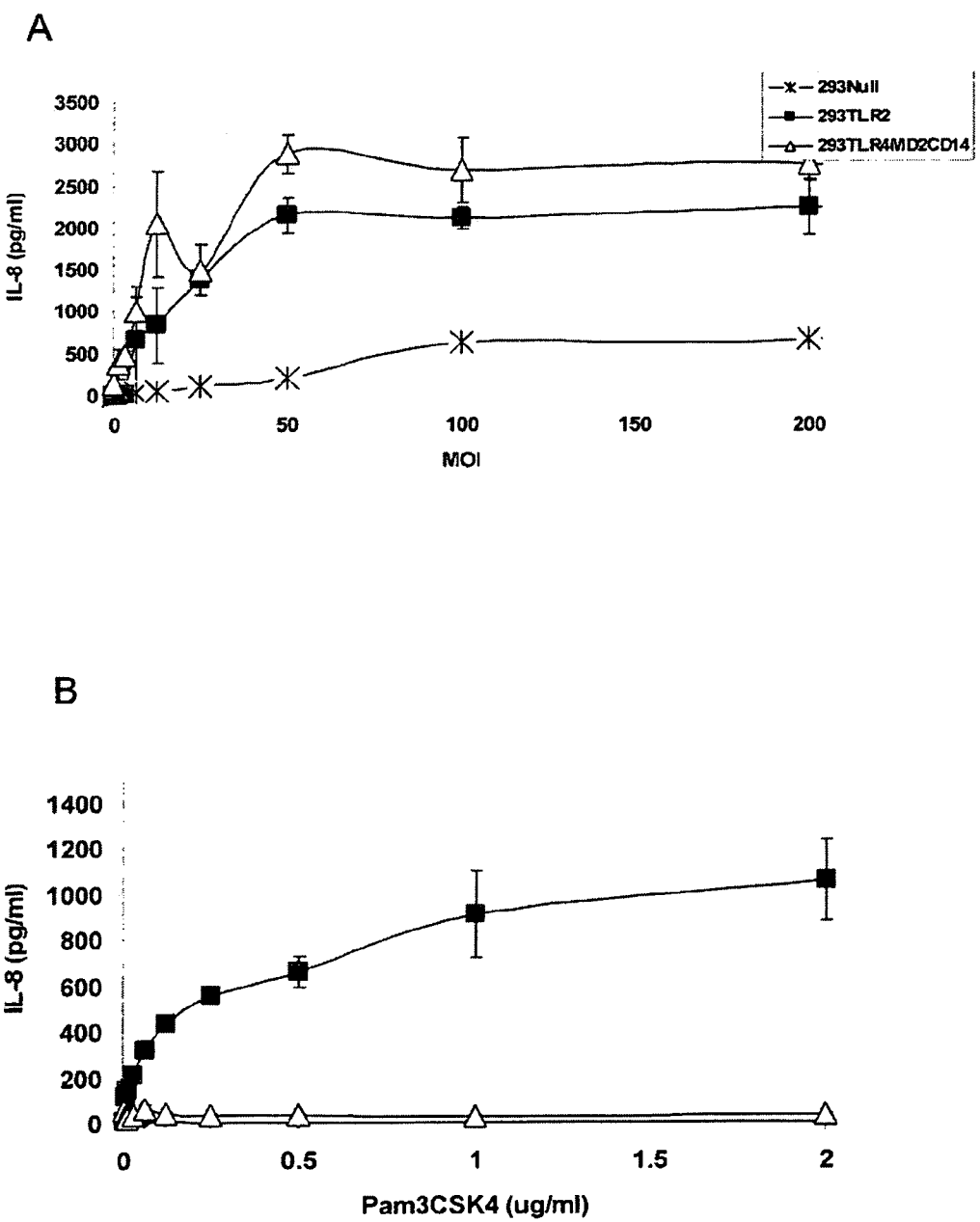
FIG. 1 illustrates stimulation of IL-8 expression from HEK293 cells as determined by ELISA. HEK293 cells stably transfected with TLR2 (■), TLR4/MD2/CD14 (Δ) or the vector control (X) were stimulated with *F. nucleatum* 12230 at different MOI values (A), Pam3CSK4 (B), and *E. coli* LPS (C) at varying concentrations. The SD values are expressed as bars above and below the geometric symbols.

Previous work showed that F. nucleatum 12230 stimulated IL-8 expression from epithelial cells. To examine the involvement of TLRs in the activation of the proinflammatory response, the ability of F. nucleatum to stimulate IL-8 expression was tested using HEK293 null cells, which lack TLR2 or TLR4, and HEK293 cells stably transfected with human TLR2 or TLR4/MD2/CD14. The expression of TLR2 and TLR4 in the stably transfected cells was verified by reverse-transcription PCR and flow cytometry using TLR2- or TLR4-specific Abs (data not shown). F. nucleatum 12230 was incubated with the 293 cells at varying multiplicities of infection (MOI; bacteria:HEK cells) for 24 h. The amount of IL-8 secreted into the culture medium was determined by ELISA. At MOI<50, F. nucleatum stimulated little or no IL-8 from HEK293-null cells but did so from both HEK293/TLR2 and HEK293/TLR4/MD2/CD14 cells in a dose-dependent manner (FIG. 1A). The induction of TLR-transfected cells reached a plateau at MOI>50, with the maximum concentration of IL-8 at between 2,000 and 3,000 pg/ml. The induction of HEK293 null cells increased slowly through a MOI of 200, with a maximum IL-8 concentration of 1,000 pg/ml (FIG. 1A). The TLR2-specific ligand Pam3CSK4 and the TLR4-specific ligand E. coli LPS only activated their respective receptors but not vice versa, indicating the specificity of the TLR activation (FIGS. 1, B and C). Taken together, these results indicate that although the expression of IL-8 in response to F. nucleatum may involve TLR-independent pathway(s), it was much enhanced in the presence of human TLR2 or TLR4.

Fetal Death Rate was Reduced in TLR4-Deficient but not in TLR2-Deficient Mice in Response to F. nucleatum 12230 Infection

Figure 2:
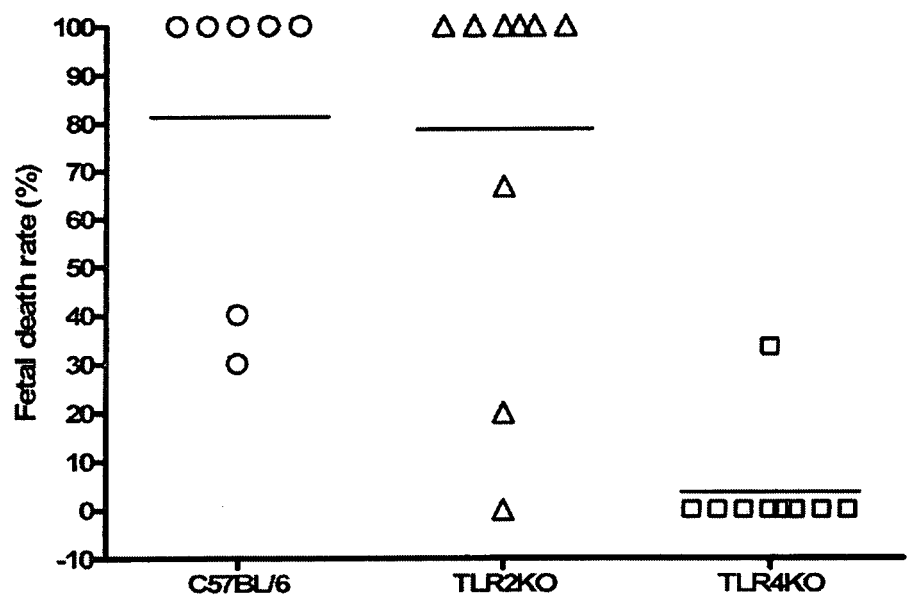
FIG. 2 illustrates birth outcome of different mouse strains in response to i.v. infection of *F. nucleatum* 12230. Approximately $3\text{-}7 \times 10^7$ CFU were injected into each pregnant mouse. The fetal death rate was expressed as the percentage of dead fetuses from the total number of pups born to each mother. Each geometric symbol represents one pregnant mouse. A, C57BL/6 (O; n=7), C57BL/6 $TLR2^{-/-}$ (Δ, n=10), and C57BL/6 $TLR4^{-/-}$ (□; n=9). B, C3H/HeN (●; n=9) and C3H/HeJ (■; n=13). The horizontal lines indicate the average fetal death rates.
Figure 2:
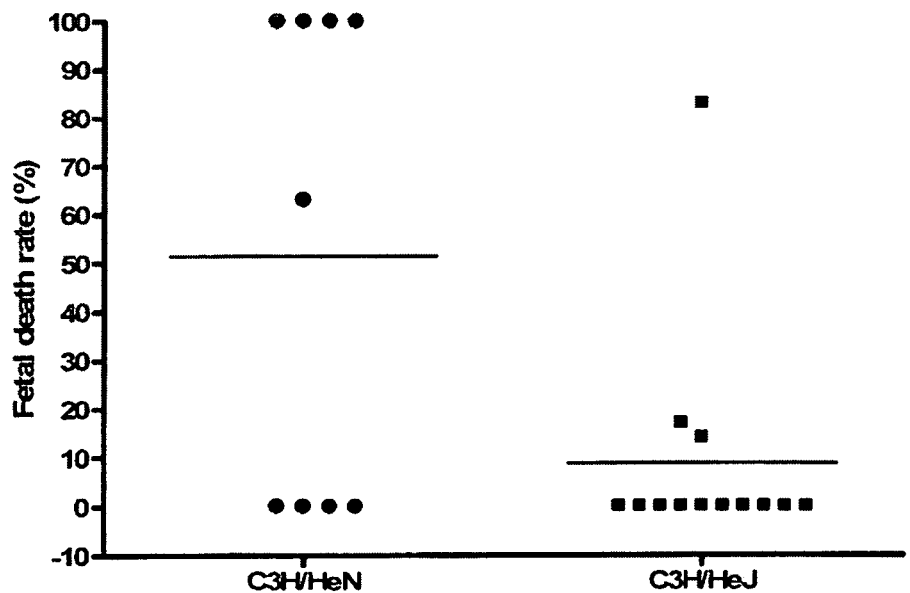

To assess the involvement of TLR2 and TLR4 in bacterial-induced fetal death, two knockout strains, C57BL/6 TLR2$^{-/-}$ and C57BL/16 TLR4$^{-/-}$, and one strain of spontaneous TLR4-deficient mice, C3H/HeJ, which carries a point mutation in the TLR4 gene, were tested along with their respective wild-type strains, C57BL/6 and C3H/HeN. An aliquot of CFU ($\sim$3-7$\times$10$^7$) of F. nucleatum 12230 were injected into each pregnant mouse through the tail vein on day 16 or 17 of gestation. Statistical analysis showed no difference between the bacterial dosages injected into each mouse strain. High fetal death rate was observed in C57BL/6 and C57BL/6 TLR2$^{-/-}$, i.e., 81.4 and 78.7%, respectively (FIG. 2A). However, a significantly lower fetal death rate of 3.7% was observed in C57BL/6 TLR4$^{-/-}$ mice (p<0.001). Similar differences also existed between C3H/HeN and C3H/HeJ mice (FIG. 2B) with a fetal death rate of 51.4% in C3H/HeN and 8.8% in C3H/HeJ (p<0.05).

Extent of F. nucleatum 12230 Colonization Differs in TLR4-Deficient C3H and C57BL/6 Mice

Figure 3:
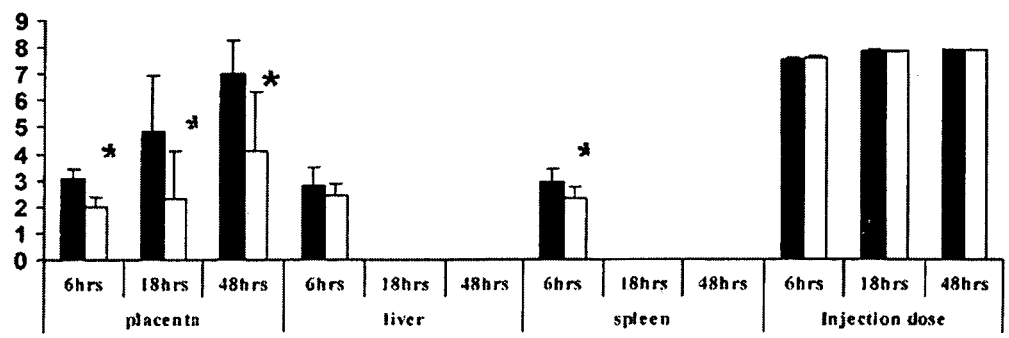
FIG. 3 illustrates kinetics of infection in the liver, spleen, and placenta of different mouse strains following the i.v.
Figure 3:
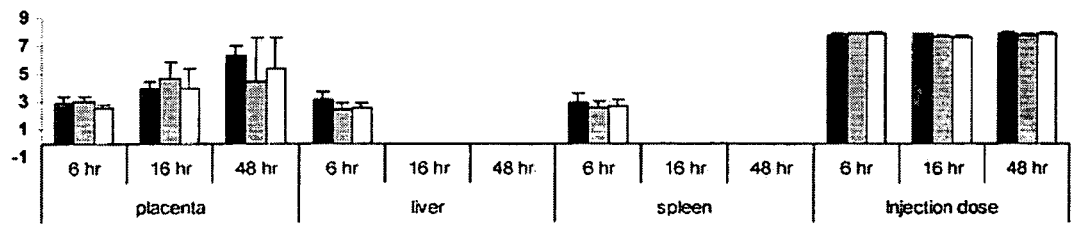

To investigate why TLR4-deficient but not TLR2-deficient mice presented improved birth outcome following F. nucleatum infection, the live bacterial titers in the liver, spleen, and placenta of the infected mice were determined at 6, 16 (or 18), and 48 h postinjection. Again, no difference was detected between the bacterial dosages injected into each mouse strain (FIG. 3). In all of the infected mice F. nucleatum 12230 was isolated from all three organs at 6 h. The bacteria proliferated in the placenta but did not persist in the liver or the spleen and were cleared from the latter two organs after 16-18 h (FIG. 3). These observations were consistent with our previous results for fusobacterial infection in pregnant outbred CF-1 mice (Han et al., (2004)). Although these general trends were consistent, differences between the wild-type and mutant C3H and C57BL/6 mice were observed. No difference in the kinetics of infection was detected between C57BL/6 TLR2$^{-/-}$, C57BL/6 TLR4$^{-/-}$, and C57BL/6 mice (FIG. 3B). In contrast, a significant difference was observed between C3H/HeN and C3H/HeJ mice (FIG. 3A). F. nucleatum 12230 colonized less in the placenta and spleen in HeJ than in HeN at 6 h postinfection (p<0.05). It also proliferated to a lesser extent in the placenta after 18 and 48 h, respectively (p<0.05). These results suggest that TLR4 may play different roles in F. nucleatum colonization in the C3H and C57BL/6 background. Alternatively, mice with total deletion of TLR-4 may have compensatory adaptations not observed in those with point mutations.

TLR4 Deficiency Led to Reduced Necroinflammatory Response in Both C3H and C57/B/6 Backgrounds

To determine the role of TLR2 and TLR4 in the placental inflammatory response to fusobacterial infection, placentas from C3H/HeN and C3H/HeJ mice were collected at 18 and 48 h postinfection, and from C57BL/6, C57BL/6 TLR2$^{-/-}$, and C57BL/6 TLR4$^{-/-}$ mice at 48 h postinfection, all from the same mice from which the bacterial titers were determined, followed by histopathological analysis. Necrosis and inflammation were apparent in the decidua, the marginal region, the labyrinth, and the membranous yolk sac of the placentas from C3H/HeN and C57BL/6 (FIG. 4). The inflammatory infiltrate was composed almost entirely of polymorphonuclear leukocytes (FIG. 4I-c,). However, they were reduced or lacking in those from the TLR4-deficient C3H/HeJ and C57BL/6 TLR4$^{-/-}$ mice despite a similar initial inoculum of F. nucleatum 12230 (FIG. 4). When the percentage of placentas with any necrosis or inflammation in different regions was calculated, the difference between the wild-type and the TLR4-deficient mice was significant (p<0.05; Table I). These results indicate that TLR4 played a pivotal role in the placental necroinflammatory response to F. nucleatum infection in both C57BL6 and C3H mice. In contrast, C57BL/6 TLR2$^{-/-}$ mice showed similar histopathology as C57BL/6 mice (Table I), suggesting the lack of TLR2 involvement in the placental inflammatory response. This was consistent with the high fetal death rate observed in the C57BL/6 TLR2$^{-/-}$ mice.

TABLE I

Summary of placental histopathological lesions of TLR4$^{+/+}$ and TLR4-deficient mice infected with F. nucleatum 12230$^a$

| | C3H/HeN | C3H/HeJ | C35/HeN | C3H/HeJ | C57BL/6 | C57B/6TLR4$^{-/-}$ | C57B/6TLR2$^{-/-}$ |
|---|---|---|---|---|---|---|---|
| Duration of infection (h) | 18 | 18 | 48 | 48 | 48 | 48 | 48 |
| No. of mothers/no. placentas | 16/49 | 8/17 | 8/17 | 7/25 | 5/17 | 8/21 | 4/13 |
| Percentage placentas positive for | | | | | | | |
| Yolk sac necrosis | 0.77 ± 0.39 | 0.07 ± 0.19* | 0.66 ± 0.48 | 0.00 ± 0.00* | 0.28 ± 0.41 | 0.00 ± 0.00* | 0.00 ± 0.00 |
| Labyrinth necrosis | 0.46 ± 0.42 | 0.11 ± 0.20 | 0.63 ± 0.52 | 0.07 ± 0.19* | 0.28 ± 0.42 | 0.00 ± 0.00* | 0.10 ± 0.20 |
| Marginal necrosis | 0.00 ± 0.00 | 0.00 ± 0.00 | 0.89 ± 0.25 | 0.61 ± 0.35 | 0.56 ± 0.46 | 0.00 ± 0.00* | 0.78 ± 0.26 |

TABLE I-continued

Summary of placental histopathological lesions of TLR4$^{+/+}$ and TLR4-deficient mice infected with *F. nucleatum* 12230[a]

|  | C3H/HeN | C3H/HeJ | C35/HeN | C3H/HeJ | C57BL/6 | C57B/6TLR4$^{-/-}$ | C57B/6TLR2$^{-/-}$ |
|---|---|---|---|---|---|---|---|
| Decidual necrosis | 0.20 ± 0.24 | 0.00 ± 0.00* | 0.48 ± 0.38 | 0.08 ± 0.14* | 0.04 ± 0.09 | 0.00 ± 0.00 | 0.33 ± 0.24 |
| Decidual PMN | 0.03 ± 0.13 | 0.00 ± 0.00 | 0.19 ± 0.29 | 0.07 ± 0.12 | 0.50 ± 0.41 | 0.00 ± 0.00* | 0.59 ± 0.33 |

[a]For each specimen, necrosis and inflammation were scored in three decidual regions (margin, center, and paracentral venous sinusoidal), three placental regions (spongiotrophoblast, labyrinth and chorioallantoic plate), and two regions of the placental membranes (yolk sac and amnion).
Data are presented as the group mean ± SD of the percentage of positive regions divided by the total number of regions sampled for each mouse.
Asterisk indicates significant difference between the mutants and the corresponding wild-type controls (*, <0.05: boldfaced pairs). OMN. Polymorphonuclear cell.

TLR4 antagonist TLR4A reduced fetal death in CF-1 mice without affecting the bacterial colonization in the placenta Synthetic TLR4A is a lipid A mimetic and an antagonist of TLR4 (Fort et al., (2005) J. Immunol. 174:6416-6423). To further test the role of TLR4 in *F. nucleatum* induced fetal death, an aliquot of 100 μg of TLR4A or an equal volume of the compound vehicle was co-injected with $1\times10^8$ CFU of bacteria into each pregnant outbred CF-1 mouse on day 16. On day 17, another dose of 100 μg of TLR4A or an equal volume of the compound vehicle was injected. The fetal death rate of the group receiving the compound vehicle and *F. nucleatum* was 92.5% while that of the group receiving TLR4A in conjunction with the bacteria was 48.2%, a near 2-fold reduction (FIG. 5; p=0.001). Histologic necrosis in both the central and paracentral decidua was also significantly decreased in mice treated with TLR4A (FIG. 6; p=0.0]). However, *F. nucleatum* colonization in the mouse placenta was unchanged (FIG. 7; p>0.05). When injected without the bacteria, TLR4A, or its vehicle, had no adverse effects on the mother or the fetuses (FIG. 5). TLR4A also had no inhibitory effect on *F. nucleatum* 12230 growth in in vitro testing.

Discussion

It was shown previously that *F. nucleatum* adhered to and invaded epithelial and endothelial cells (Han et al., (2004); Han et al., (2000)). The organism was also a strong inducer of the proinflammatory chemokine IL-8 (Han et al., (2000); Darveau et al., (1998) Infect. Immun. 66:1660-1665). These phenomena help explain the marked inflammation associated with colonization of the oral and uterine cavities by this organism (Hill et al., (1998); Han et al., (2004)). Intravenous injection of *F. nucleatum* into pregnant mice induced preterm and term fetal death (Han et al., (2004)). The pregnant murine model mimicked human intrauterine infection in the following aspects: 1) the infection was localized within the fetoplacental unit rather than spreading systemically; 2) the infection initiated in the decidua and spread to the AF, fetal membranes, and the fetuses; and 3) the infected murine placentas exhibited a strong neutrophil-predominant necroinflammatory response. Previous studies have suggested that innate rather than adaptive immune responses are the primary defense against intrauterine infection (Redline et al., (1987) J. Clin. Invest. 79:1234-1241). Because TLRs are key components of the innate immune response, their involvement in fusobacterial-induced fetal death in mice was investigated.

The in vitro studies demonstrated that at low MOI values (<50), *F. nucleatum* induced IL-8 expression predominantly via TLR2 and TLR4, each following a dose-dependent pattern (FIG. 1). At higher MOI values (>50), the TLR2- and TLR4-dependent induction reached a plateau and TLR2- and TLR4-independent pathway(s) appeared to be involved, albeit to a lesser extent (FIG. 1). These results suggest that *F. nucleatum* is capable of activating multiple pattern recognition receptors, including but not limited to TLR2 and TLR4.

Expression of both TLR2 and TLR4 has been detected in term human placentas (Holmlund et al., (2002) Immunology 107: 145-151). However, they appear to function differently, at least during the first trimester (Holmlund et al., (2002)). Whereas the activation of TLR4 in the trophoblastic cells induced cytokine production, the activation of TLR2 induced apoptosis (Abrahams (2004) J. Immunol. 173:4286-4296). The current study also suggests different roles for TLR2 and TLR4 in murine pregnancy. At the dosage tested *F. nucleatum* 12230 induced significantly reduced fetal death and placental inflammation in TLR4-deficient mice in both the C57BL/6 and C3H backgrounds as compared with the TLR4$^{-/-}$ mice. The fact that the reduction of fetal death was observed in two different TLR4-deficient mouse strains confirmed the attribution to TLR4 rather than to the different genetic backgrounds of the strains (see below). The current study did not find TLR2 to be critically involved in the pathogenesis of *F. nucleatum*-induced intrauterine infection in mice. No significant difference was observed between the wild-type and TLR2-deficient mice in terms of the fetal death rate, bacterial colonization, or placental inflammatory response. This could be due to the lack of TLR2 expression in the mouse placenta (Harju et al., (2001) Pediatr. Res. 49:81-83). Whether or not TLR2 plays a role in adverse pregnancy outcome in humans needs further investigation.

The improved birth outcome in the TLR4 deficient mice could be due to one or both of the following mechanisms: 1) the inhibition of bacterial colonization and proliferation in the mouse placentas; and 2) the reduction of the inflammatory response to bacterial infection. Assessing the relationship between bacterial titers and necroinflammatory changes in animals allowed us to test both of these scenarios. In both the C57,BL/6 and C3H mice *F. nucleatum* colonized within the placenta without causing systemic infections (FIG. 3), similarly as previously reported in the outbred mice (Han et al., (2004)). Interestingly, in C3H/HeJ mice fusobacterial colonization was significantly reduced in the placenta and spleen compared with in C3H/HeN, suggesting that the TLR4 deficiency affected bacterial colonization (FIG. 3). This contrasted with the previous observations that *Leptospira* and *E. coli* colonized more in the-liver in C3H-HeJ than in the wild-type C3H mice (Cross et al., (1995) J. Clin. Invest. 96:676-686; Viriyakosol et al., (2006) Infect. Immun. 74:887-895). In the C57BL/6 mice, however, neither TLR2 nor TLR4 deficiency exhibited an effect on fusobacterial colonization (FIG. 3). The discrepancy observed between C3H and C57BL/6 mice may be due to the different genetic backgrounds of the strains, which has been reported before in other murine infection models. For instance, the BALB/c IL-12 knockout mice were highly susceptible to infection by *Helicobacter pylori*, but the C57BL/6 IL-12 knockout mice were resistant to infection by the same organism (Panthel et al., (2003) Infect. Immun. 71:794-800). Immunohistochemical staining (data not shown) verified our previous data showing that necrosis and inflammation colocalized with *F. nucleatum* colonization in the placenta and uterus of genetically intact mice. These inflammatory changes would at least in part be expected to depend on the engagement of local TLRs on placental cells by pathogen-associated molecular patterns expressed by *F. nucleatum* and might be decreased in mice lacking the expression of specific TLRs. We observed that irrespective of the genetic background, TLR4 deficiency resulted in reduced necroinflammatory response to fusobacterial infection in the placenta (FIG. 4 and Table 1). These results suggest that TLR4 promoted fetal death through stimulation of the inflammatory response rather than by influencing the bacterial colonization.

The validity of this conclusion was further tested by using the synthetic TLR4 antagonist TLR4A, which had been shown to prevent the expression of proinflammatory genes and reduce inflammatory bowel disease in mice (Fort et al., (2005)). The injection of TLR4A into *F. nucleatum*-infected pregnant CF-1 mice led to a near 2-fold reduction in the fetal death rate (FIG. 5). Outbred mice were chosen for this test so that the effects of the genetic background of different inbred strains could be eliminated. TLR4A exhibited no bactericidal effect in vitro. *F. nucleatum* colonized the placentas to a similar extent in both the treatment and the control group. Thus, the reduction of fetal death was not caused by the inhibition of bacterial colonization or the killing of the bacteria. Histopathological analysis showed a significant reduction of decidual necrosis in response to fusobacterial infection in the TLR4A treatment group compared with the placebo group (p=0.01), confirming that TLR4A reduced the necroinflammatory response.

It should be pointed out that, under our test conditions, fetal death was reduced by TLR4A treatment but it was not eliminated or reduced to a similar extent as that seen in the TLR4-deficient mice. Two non-mutually exclusive possibilities exist. The first possibility is that TLR4A did not completely block TLR4 activation. Two consecutive doses of 0.1 mg of TLR4A per pregnant mouse per injection were administered. It is not known whether both dosages were necessary and whether higher doses or more frequent injections would improve the birth outcome further. The second possibility is that *F. nucleatum* may contribute to fetal death through additional TLR4-independent pathways.

The discovery that TLR4A treatment improves pregnancy outcome in mice is significant in several ways. First, it confirmed that the placental inflammatory response plays a key role in murine fusobacterial infection, similar to the intrauterine infection in humans. Thus, it validates the use of the pregnant murine model to study the pathogenesis of fusobacterial-induced adverse pregnancy outcome. Second, because placental TLR4 expression has been shown to increase in women with PTB and chorioamnionitis compared with those with PTB but without chorioamnionitis (Kumazaki et al., (2004) Hum. Pathol. 35:47-54), TLR4A may be useful in the treatment of these infections in humans. Third, the results indicate the importance of bacterial LPS in the pathogenesis in intrauterine infection. TLR4A may be useful for the treatment of infections caused by other Gram-negative organisms. Fourth, our results may explain at least in part why antibiotic therapies have not been successful at reducing the preterm birth rate (Andrews et al., (2003) Semin. Preinatol. 27:231-238; Andrews et al., (2006) Am. J. Obstet. Gynecol. 194:617-623; Andrews et al., (2003) Obstet. Gynecol. 101:847-855). Although antibiotics may kill the bacteria, they are unable to eradicate the dead microorganisms that are capable of inducing inflammatory responses. Based on our findings, antibiotic therapies in conjunction with anti-inflammatory therapies are more likely to succeed in improving birth outcome than either therapy alone.

The efficacy of TLR4A in this murine model adds to the scarce arsenal of potential agents for the prevention of PTB. Although 17-α hydroxyprogesterone caproate has been used in pregnant women with a prior PTB history, this compound was recently found to cause significant maternal morbidity in mice (Elovitz et al., (2006) Am. J. Obstst. Gynecol. 195:1004-1010). TLR4A, in contrast, did not exhibit any detectable adverse effect on either the fetus or the mother in our study. Thus, it is a promising anti-inflammatory agent for the treatment and prevention of adverse pregnancy outcomes. As indicated above, because TLR4A is nonbactericidal, it probably will achieve a maximal protective effect as an adjunct to specific antimicrobial therapy.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, the following is claimed:

1. A method of inhibiting bacterial induced fetal death in a pregnant subject at risk of developing placental inflammation response associated with intrauterine bacterial infection, the method comprising:
    administering to the pregnant subject with intrauterine bacterial infection a therapeutically effective amount of a toll-like receptor 4 antagonist, wherein the therapeutically effective amount is an amount effective to reduce intrauterine inflammation and inhibit bacterial induced fetal death in the pregnant subject.

2. The method of claim 1, the toll-like receptor 4 antagonist comprising a monophosphoryl lipid A analog.

3. The method of claim 1, the toll-like receptor 4 antagonist comprising an aminoalkyl-glucosaminide-phosphate (AGP).

4. The method of claim 3, the AGP comprising the structure:

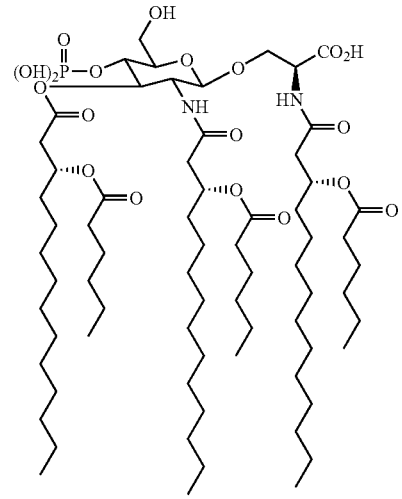

or a pharmaceutically acceptable salt or phosphate ester thereof.

5. The method of claim 1 wherein the toll-like receptor 4 antagonist is administered to the subject by intravenous infusion.

6. The method of claim 1, wherein the toll-like receptor 4 antagonist is administered to the subject topically.

7. The method of claim 1, wherein the bacterial induced fetal death comprising gram negative bacterial induced fetal death.

8. The method of claim 7, wherein the gram negative bacteria is *fusobacterium nucleatum*.

\* \* \* \* \*